(12) United States Patent
Fischer et al.

(10) Patent No.: US 6,309,372 B1
(45) Date of Patent: Oct. 30, 2001

(54) INTEGRATED MIXING AND DISPENSING APPARATUS

(75) Inventors: Dan E. Fischer, Sandy; Bruce S. McLean, Salt Lake City, both of UT (US)

(73) Assignee: Ultradent Products, Inc., South Jortlan, UT (US)

( * ) Notice: Subject to any disclaimer, the term of this patent is extended or adjusted under 35 U.S.C. 154(b) by 0 days.

(21) Appl. No.: 09/356,009

(22) Filed: Jul. 16, 1999

(51) Int. Cl.⁷ .................................................. A61M 37/00
(52) U.S. Cl. ................................ 604/82; 604/416; 433/90
(58) Field of Search .......................... 604/82, 83, 86, 604/88, 187, 218, 220, 91, 416, 191, 411, 226, 228, 221; 222/83, 85, 137, 145.6; 433/88–90

(56) References Cited

U.S. PATENT DOCUMENTS

| | | | |
|---|---|---|---|
| 5,328,462 | 7/1994 | Fischer | 604/82 |
| 5,643,206 | 7/1997 | Fischer | 604/82 |
| 5,665,066 | 9/1997 | Fischer | 604/82 |
| 5,697,903 | 12/1997 | Fischer | 604/82 |
| 5,899,881 * | 5/1999 | Grimard et al. . | |
| 5,925,019 * | 7/1999 | Ljungquist . | |
| 5,935,101 * | 8/1999 | Kato et al. . | |

* cited by examiner

Primary Examiner—Anhtuan T. Nguyen
(74) Attorney, Agent, or Firm—Workman, Nydegger & Seeley (57) ABSTRACT

A syringe apparatus for mixing and delivering a two-part material has (i) a syringe barrel and a plunger. The apparatus also has a paddle slidably coupled to the plunger. A distal insertion end of the plunger has a slot therein. A proximal end of the paddle is slidably coupled within the slot. The paddle is movable between an extended position and a contracted position with respect to the plunger. Upon placing material into the barrel, such as through an opening in the wall of the barrel, the paddle can be employed to mix the material. After such mixing, the plunger is pressed further into the barrel without removing the paddle, thereby expressing the mixed material from the barrel and compressing the paddle into the slot of the plunger.

27 Claims, 7 Drawing Sheets

FIG. 7

INTEGRATED MIXING AND DISPENSING APPARATUS

BACKGROUND OF THE INVENTION

1. The Field of the Invention

This application is directed to methods and devices for mixing and dispensing medical and dental compositions. More particularly, the application is directed to methods and devices for mixing and dispensing multi-part medical and dental compositions.

2. The Relevant Technology

Many modern formulations are packaged in two parts, often known as A and B components. Upon mixing, these A and B components typically undergo a chemical reaction which causes the resultant composition to "set up" in some desired manner. In the dental field, for example, several two-part formulations currently enjoy wide use such as glass ionomer cements and resinous luting cements. Dental impression materials are also typically made using A and B components.

In order to function properly, it is important that the A and B components of these two component systems be mixed together rapidly and thoroughly and in the right proportions. Failure to mix rapidly can result in loss of valuable working time with the resultant composition, and can impact the ability to obtain a thorough mix as the composition begins to set up unevenly. Failure to mix thoroughly can result in a composition having less than optimum characteristics. For example, if a poorly mixed composition is used as a cement, it is possible that portions of the cement will fail to reach the chemical strength required for a long-term bond.

Problems of obtaining rapid and uniform mixing are often complicated by differences in the A and B components. Often it is necessary to mix two liquids, while other times it is necessary to mix a powder with a liquid. Sometimes there are equal amounts of the A and B components, but other times there is more of one component than another. Additionally, the two components may have similar viscosities or widely differing viscosities.

The primary method employed for mixing A and B components has been simple mechanical mixing, through the use of a mixing bowl or pad and a stir instrument such as a spatula. This method tends to be somewhat messy and time consuming. It also is difficult at times to gauge whether the mixing has been sufficiently thorough.

It is also difficult in some instances to prevent formation of small air bubbles in the mixed composition. During the mixing process itself, the stirring action of the spatula, or similar mixing instrument, introduces and causes air bubbles to be entrapped within the mixed composition. Such entrapped air bubbles are usually detrimental.

Further, most dental compositions are ultimately dispensed from a syringe in order to control the amount dispensed, to permit precise placement of the dental composition and to prevent premature evaporation of constituents of the composition. This generally requires placement of the mixed compositions into a syringe. Additional air can become entrapped during this step.

Additionally, the simple process of mixing the components on a pad or in a bowl and then transferring them to a syringe takes time; this can lessen the available working time to actually utilize the composition. It is not uncommon for so much time to pass during the mixing and syringe-loading steps that the mixed composition becomes effectively unusable.

In an effort to overcome the time delays and the mess inherent in the approach set forth above involving mixing on a pad or in a bowl followed by loading into a syringe, attempts have been made to mix materials directly from a syringe or from a caulking gun. These attempts have involved the use of specially formed tips which effect some mixing as material is dispensed from the syringe or caulking gun. Although useful from the standpoint of minimizing the amount of time used to effect the mixing of A and B components, incomplete mixing is common.

According to one technique, A and B components are loaded in side-by-side fashion within a syringe barrel, such as with a dual barrel apparatus disclosed in U.S. Pat. No. 5,697,903 after which a mixer is inserted into the syringe barrel to mix the components. Following such mixing, the mixer is removed from the barrel and discarded. A plunger is then loaded into the syringe barrel to express the mixed material out of the syringe barrel. This technique requires that the mixer be initially placed into the barrel, then removed therefrom, often having residue of the mixture thereon, after which the plunger is placed into the barrel. These steps require the use of time, which is of the essence during the procedure.

What is therefore needed is an improved method and apparatus for mixing and dispensing compositions, particularly multi-part compositions.

SUMMARY AND OBJECTS OF THE INVENTION

It is therefore an object of the invention to provide improved methods and apparatuses for mixing and dispensing compositions.

It is another object of the invention to provide improved methods and apparatuses for mixing and dispensing multi-part compositions.

It is another object of the invention to provide improved methods and apparatuses for mixing and dispensing multi-part compositions without requiring the continual insertion and removal of different components.

Another object of the present invention is to provide improved methods and apparatuses for mixing multi-component compositions that substantially prevent the entrapment of air bubbles in the mixed compositions.

Yet another object of the present invention is to provide methods and apparatuses for mixing multi-component compositions which effect rapid and thorough mixing.

The present invention relates to apparatuses for mixing and dispensing a composition. An apparatus of the present invention essentially comprises: (i) a syringe barrel; (ii) a plunger having an end that is receivable within the syringe barrel; and (iii) a paddle slidably coupled to the plunger. A distal insertion end of the plunger has a slot therein. A proximal end of the paddle is slidably coupled within the slot. The paddle is movable between an extended position and a contracted position with respect to the plunger.

The extended paddle is used to mix material within the barrel of the syringe. When mixing is complete, the plunger is pressed further into the barrel. This process expels material through a distal opening of the barrel onto a selected location and compresses the paddle into the contracted position.

Upon inserting the distal insertion end of the plunger partially within the barrel and twisting the plunger while the paddle is in the extended position, the paddle twists, thereby mixing a material deposited in the barrel. The plunger is then pressed further into the barrel, thereby expressing the mixed material through the distal opening of the syringe barrel. At least a portion of the paddle slides into the slot of the plunger as the plunger is pressed into the barrel.

As a result, a two-part composition initially deposited into the barrel can be first mixed, then delivered from the barrel. This mixing and delivery dynamic can be achieved without requiring the insertion and removal of a separate mixer before a plunger is inserted.

In a preferred embodiment, the syringe barrel has an intermediate opening extending through the barrel side wall. The intermediate opening is located between the proximal and distal openings of the barrel. The intermediate opening enables a practitioner to load a two-part material through the wall of the barrel while the distal tip of the plunger is inserted through the proximal opening of the barrel. After loading the barrel through the intermediate opening, the paddle can then be used to mix the loaded material. The plunger is then pressed further within the barrel to force the mixed material from the barrel without requiring the paddle to be first removed from the barrel.

Thus, as one advantage to the apparatus of the present invention, it is possible to use the plunger and paddle without requiring the continual insertion and retraction of different instruments. The apparatus of the present invention enables a practitioner to mix a material, then express the material quickly without having to remove a separate mixer.

As another advantage of the apparatus of the present invention, complete mixing can be achieved through twisting and/or back and forth movement of the paddle. The paddle is also perforated to enhance complete mixing. Air bubbles are expelled through the intermediate opening as the plunger compresses material within the barrel. Thus, the invented apparatus is efficient, mixes material completely, and conserves procedural time.

These and other objects, features and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings listed hereinbelow.

DETAILED DESCRIPTION OF THE PREFERRED EMBODIMENTS

Figure 1:
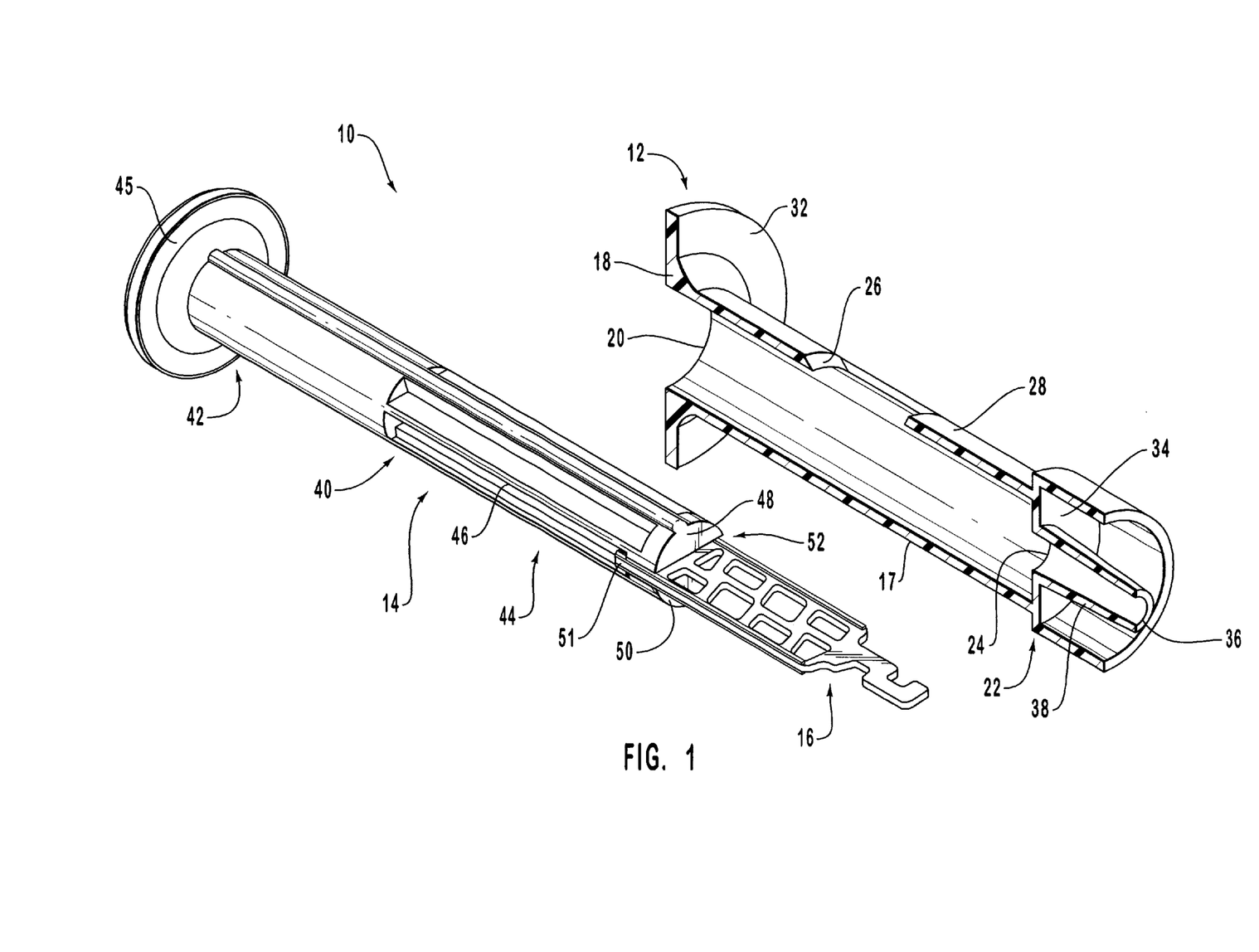
FIG. 1 is a perspective view of a mixing and dispensing apparatus of the present invention wherein a syringe barrel of the apparatus is shown in a cutaway view.
Figure 6:
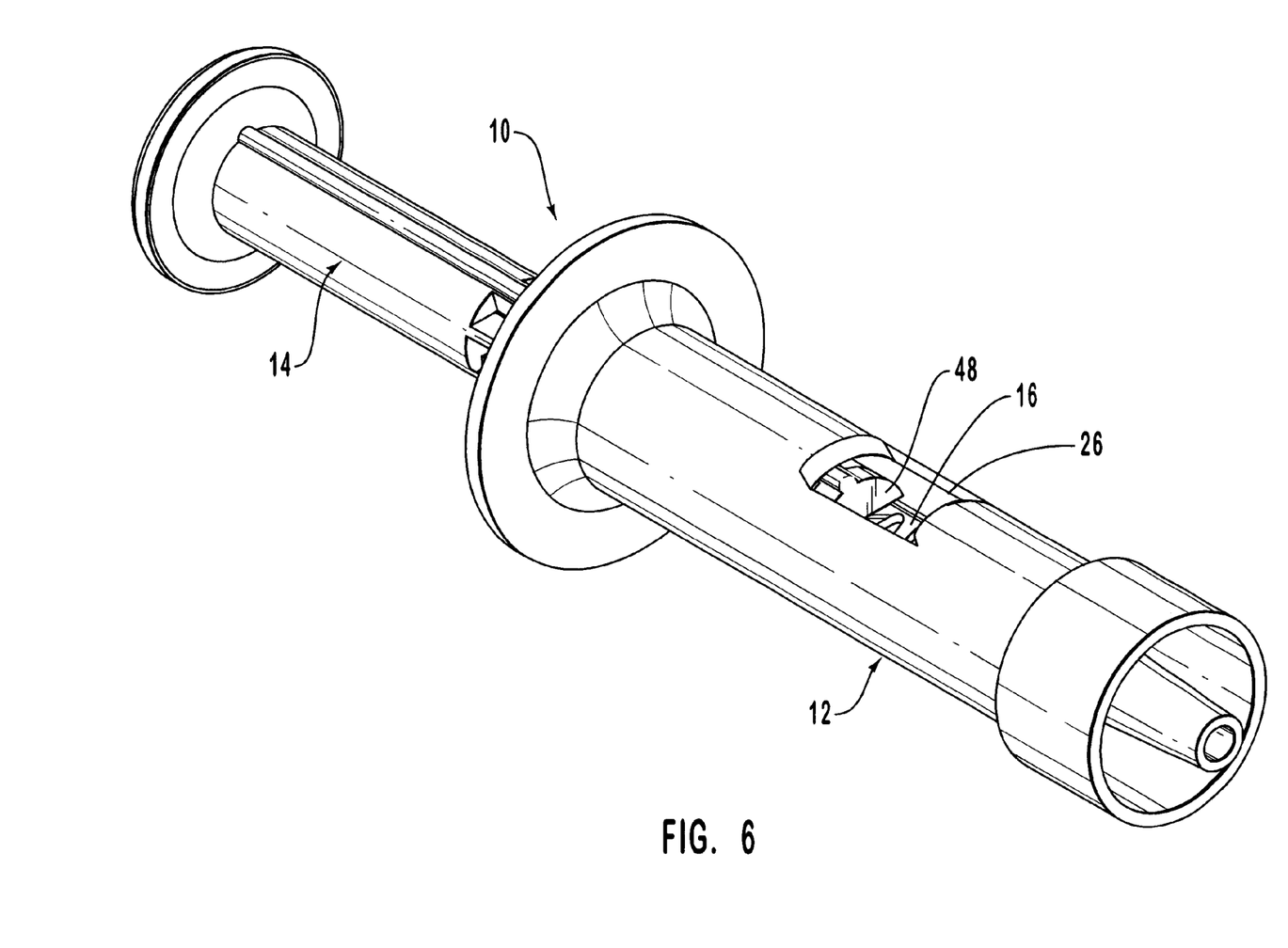
FIG. 6 is an assembled, perspective view of the apparatus of FIG. 1.

With reference now to FIG. 1, an example of an apparatus 10 for mixing and dispensing a composition of the present invention is shown. Apparatus 10 comprises: (i) a syringe barrel 12 for receiving a composition; (ii) a plunger 14; and (iii) a paddle 16 movably coupled to plunger 14. Apparatus 10 is also shown assembled in a perspective view in FIG. 6.

As shown in FIG. 1, plunger 14 and paddle 16 are configured to interact such that a composition disposed within barrel 12 can initially be mixed by moving paddle 16, e.g., by twisting paddle 16 and/or moving paddle 16 back and forth within barrel 12. After the composition is mixed by paddle 16, the composition can then be delivered by pressing against plunger 14.

Barrel 12 is shown in a cutaway view in FIG. 1. Barrel 12 has a tubular barrel body 17. Tubular body 17 has a proximal end 18 having a proximal opening 20 therethrough and a distal end 22 having a distal opening 24 therethrough. Barrel 12 further has an intermediate opening 26 extending through wall 28 of tubular barrel body 17 and located between proximal and the distal openings 20, 24. A composition to be mixed within and delivered from barrel 12 can be inserted into barrel 12 through opening 26. The composition can then be mixed by paddle 16 and delivered through distal opening 24 by pressing against plunger 14. Optionally, a composition to be mixed within a barrel can be added through the proximal opening of a barrel which does not have an intermediate opening.

In the embodiment shown, a distal face 34 is coupled to distal end 22 of barrel body 17. Distal face 34 has opening 24 extending therethrough.

A proximal circular gripping flange 32 is coupled to proximal end 18 of tubular barrel body 17. A distal tubular tip 38 extends from face 34 concentrically with opening 24. Tip 38 is in fluid communication with barrel body 17. Tip 38 has a distal opening 36 extending therethrough. Upon pressing plunger 14 through tubular body 17 of barrel 12, a composition in tubular body 17 flows through tubular tip 38 and is delivered to a desired location through distal opening 36 of tip 38.

Plunger 14 comprises an elongate body 40 having a proximal gripping end 42 and a distal insertion end 44. Proximal end 42 has a gripping flange 45 coupled thereto. Distal insertion end 44 is receivable within barrel 12. Distal insertion end 44 of elongate body 40 has a slot 46 extending therethrough. Slot 46 in distal insertion end 44 extends between upper and lower fingers 48, 50 of distal insertion end 44.

Proximal end 51 of paddle 16 is received between fingers 48, 50 within slot 46. Proximal end 51 is slidably coupled within slot 46 and slides back and forth within slot 46. Thus, paddle 16 selectively slides between an extended position and a contracted position with respect to plunger 14. In the extended position, shown in FIG. 1, paddle 16 is able to mix a composition within barrel 12. In the contracted position (FIG. 5c), paddle 16 is moved proximally within slot 46 with respect to the extended position. As plunger 14 slides within barrel 12, distal tip 52 of plunger 14 presses against material disposed within barrel 12, forcing material through opening 36. Upon contacting distal face 34, paddle 16 contracts from the extended position to the contracted position.

Figures 2, 2A, 2B:
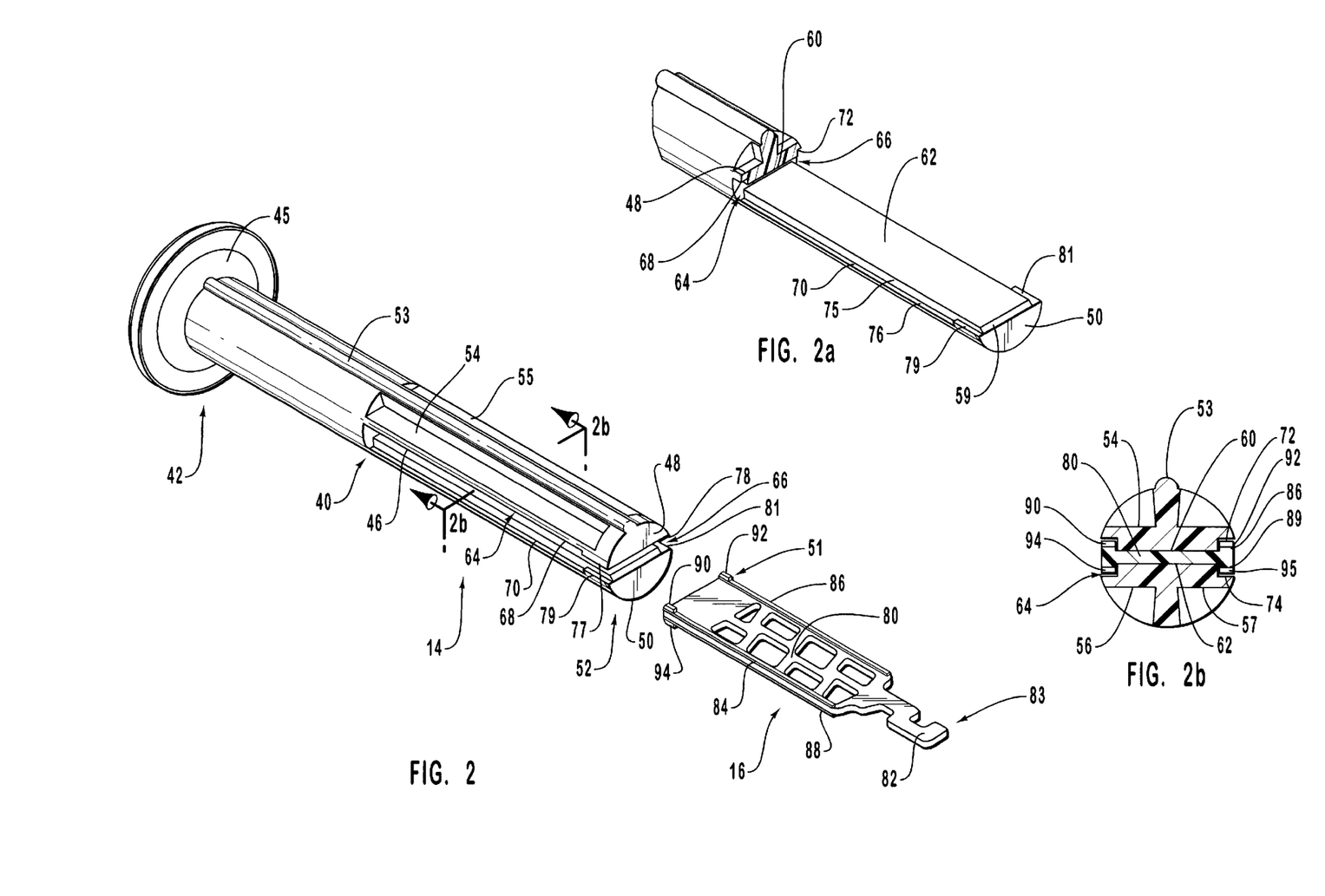
FIG. 2 is an exploded perspective view of the plunger and mixing paddle of the apparatus of FIG. 1.
FIG. 2a is a cutaway view of the plunger of the apparatus of FIG. 1.
FIG. 2b is a cross sectional view of the plunger of FIG. 1, showing the upper and lower fingers of the plunger with the paddle slidably disposed therebetween.

With reference now to FIG. 2, plunger 14 and paddle 16 are shown in an exploded view. In the embodiment shown, a longitudinally oriented rib 53 extends along body 40. Rib 53 is configured to contact the interior surface of barrel 12, causing fingers 48, 50 to be compressed against paddle 16. The amount of compression of fingers 48,50 onto paddle 16 is preferably sufficient to enable a practitioner to move paddle 16 longitudinally into a two part material deposited within barrel 12 while nevertheless allowing paddle 16 to slide at least partially into plunger 14 when plunger 14 is pressed into barrel 12 with sufficient force to contract paddle 16.

Rib 53 is an example of compressing means for compressing the fingers of the plunger against the paddle. Additional examples of such compressing means include a knob, a protuberance, or another member disposed on one or more fingers 48 or 50. The knob, protuberance, or other member may be circular, rounded, square shaped, or have another configuration which accomplishes the purpose of compressing fingers 48, 50 against paddle 16.

Figure 3:
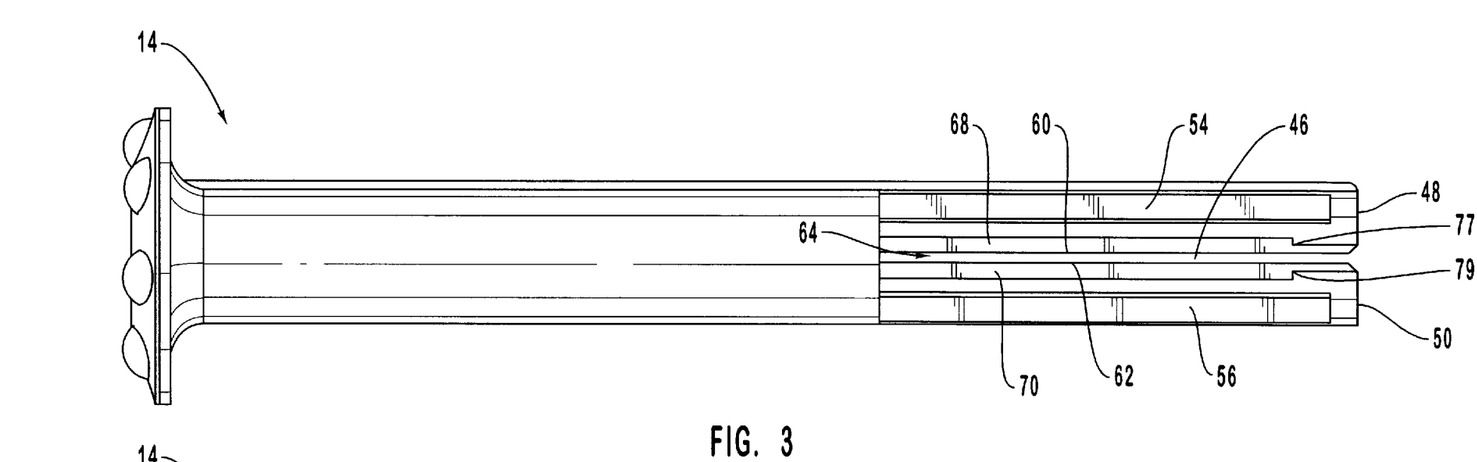
FIG. 3 is a side view of the plunger of the apparatus of FIG. 1.
Figure 4:
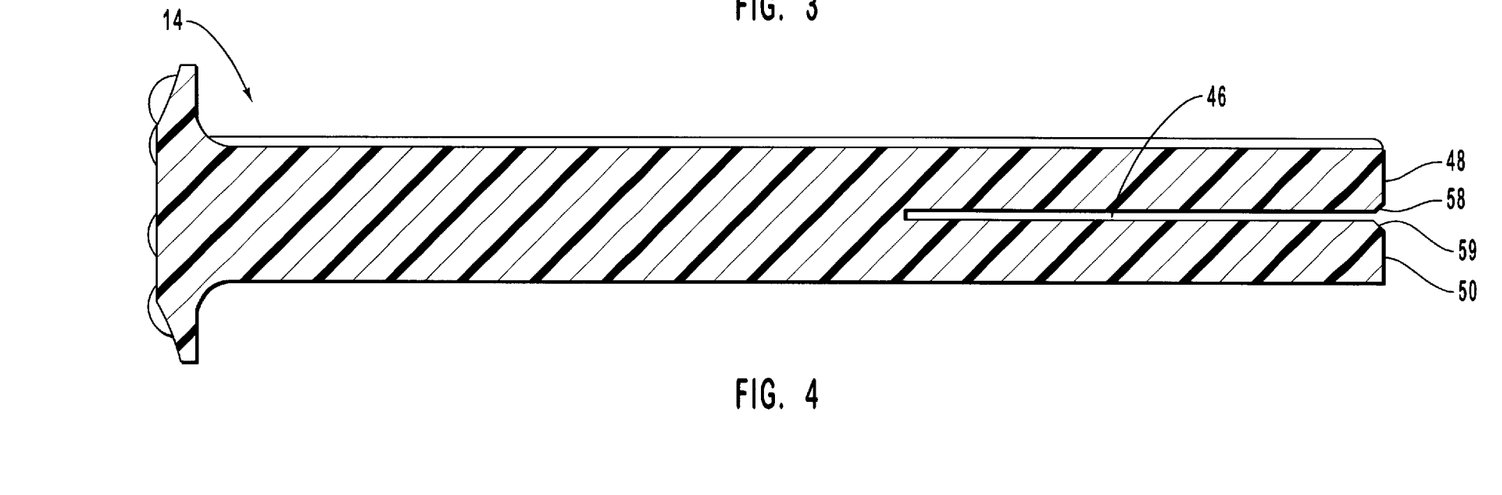
FIG. 4 is a cross-sectional side view of the plunger of the apparatus of FIG. 1.

FIG. 2a is a cutaway view of upper finger 48 and a view of lower finger 50 of the present invention, while FIG. 2b is a cross sectional view of upper finger 48 and lower finger 50 with paddle 16 therein. FIGS. 3 and 4 demonstrate side and cross sectional views of plunger 14, respectively.

As shown in FIGS. 2–2b, 3 and 4, fingers 48 and 50 are configured to collectively slidably engage paddle 16. Each finger 48, 50 preferably has one, and most preferably has a plurality of longitudinally extending grooves therein to decrease the mass of the finger and increase the flexibility thereof. For example, distal finger 48 has grooves 54, 55 therein. Finger 50 also has a plurality of longitudinal grooves 56, 57 (FIG. 2b) therein configured like grooves 54, 55 of finger 48. This configuration enables upper and lower fingers 48, 50 to be flexed apart such that paddle 16 can be inserted between fingers 48, 50 during assembly and such that fingers 48, 50 respond to a desired compressing means, such as rib 53, while sliding in barrel 12. Fingers 48, 50 have respective tapered face portions 58, 59 to thereby allow paddle 16 to be conveniently pressed between fingers 48, 50 during assembly.

In order to retain proximal end 51 of paddle 16 within slot 46 between fingers 48, 50, while nevertheless enabling sliding longitudinal movement of paddle 16, slot 46 is configured to slidably receive proximal end 51 and to arrest the longitudinal movement of proximal end 51 when proximal end 51 is extended within slot 46. Slot 46 is defined by a central sliding surface 60 of upper finger 48, a central sliding surface 62 of lower finger 50, and by first and second opposing races 64, 66. First race 64 is defined by first upper race portion 68 and first lower race portion 70. Second race 66 is defined by second upper race portion 72 and second lower race portion 74. The race portions are integral portions of the respective fingers and are recessed compared with the respective sliding surfaces. Proximal end 51 of paddle 16 is configured to be slidably coupled to first and second races 64, 66 such that the movement of paddle 16 is substantially linear.

First and second opposing upper stops 77, 78 are disposed in respective first and second opposing upper race portions 68, 70. First lower stop 79 is disposed in first lower race portion 72, while second lower stop 81 is disposed in the opposing second lower race portion 74. Upper and lower stops 77, 78, 79, 81 are preferably integral portions of respective fingers. Upper and lower stops 77, 78, 79, 81 prevent paddle 16 from sliding out of slot 46 by contacting the tabs of paddle 16, which as discussed hereinbelow are located at its proximal end. Stops 77, 78, 79, 81 thus arrest the movement of paddle 16 along the longitudinal axis of plunger 14.

Paddle 16 comprises a substantially planar main body 80 having proximal end 51 and a distal end 83. Main body 80 of paddle 16 is perforated to enhance mixing of a composition by paddle 16. Distal end 83 preferably comprises a distal tip 82 in the shape of a hook, for example, extending therefrom. Hook-shaped distal tip 82 can mix material which is in tip 38 of barrel 12 by being moved in a twisting motion during mixing.

First and second opposing upper side panels 84, 86 protrude from respective sides of planar main body 80. Panels 84, 86 slide in respective opposing first and second races 64, 66. Similarly, first and second lower side panels 88, 89 protrude from respective opposing sides of planar main body 80 for sliding in respective opposing first and second races 64, 66. By sliding in races 64 and 66, panels 84, 86, 88 and 89 maintain main body 80 between upper and lower fingers 48, 50 and prevent substantial side to side movement of paddle 16 as proximal end 51 of paddle 16 slides longitudinally within slot 46. Thus, panels 84, 86, 88 and 89 ensure substantially linear movement of paddle 16 within slot 46.

Opposing first and second upper tabs 90, 92 of paddle 16 extend from respective panels. Tabs 90, 92 slide within respective opposing upper race portions 68, 70 and are prevented from sliding out of slot 46 by respective opposing first and second upper stops 77, 78 of finger 48. Opposing first and second lower tabs 94, 95 of paddle 16 extend from respective lower panels 84, 89 and slide within respective opposing lower race portions 72, 74. First lower tab 94 and second lower tab 95 are prevented from sliding out of slot 46 by respective opposing first lower stop 79 and second lower stop 81. The proximal tips of the tabs may be tapered for convenient movement of the tabs past the stops of plunger 14 during assembly.

One embodiment of means for slidably coupling a proximal end of a paddle within a slot thus comprises (i) a slot such as slot 46 being configured to slidably receive a proximal end of a paddle such that the proximal end of the paddle slides longitudinally within the slot; and (ii) means for arresting the longitudinal movement of the proximal end of the paddle within the slot.

It will be also appreciated from the foregoing that one embodiment of means for arresting the longitudinal movement of a proximal end of a paddle within a slot of the present invention comprises (i) the plunger (e.g., plunger 14) having at least one stop located within the slot; and (ii) the paddle (e.g., paddle 16) having at least one tab configured to selectively engage the stop. The one or more stops and one or more corresponding tabs may have a variety of different configurations as long as the tabs and stops selectively interface to arrest longitudinal movement of the paddle.

Figures 5A, 5B, 5C:
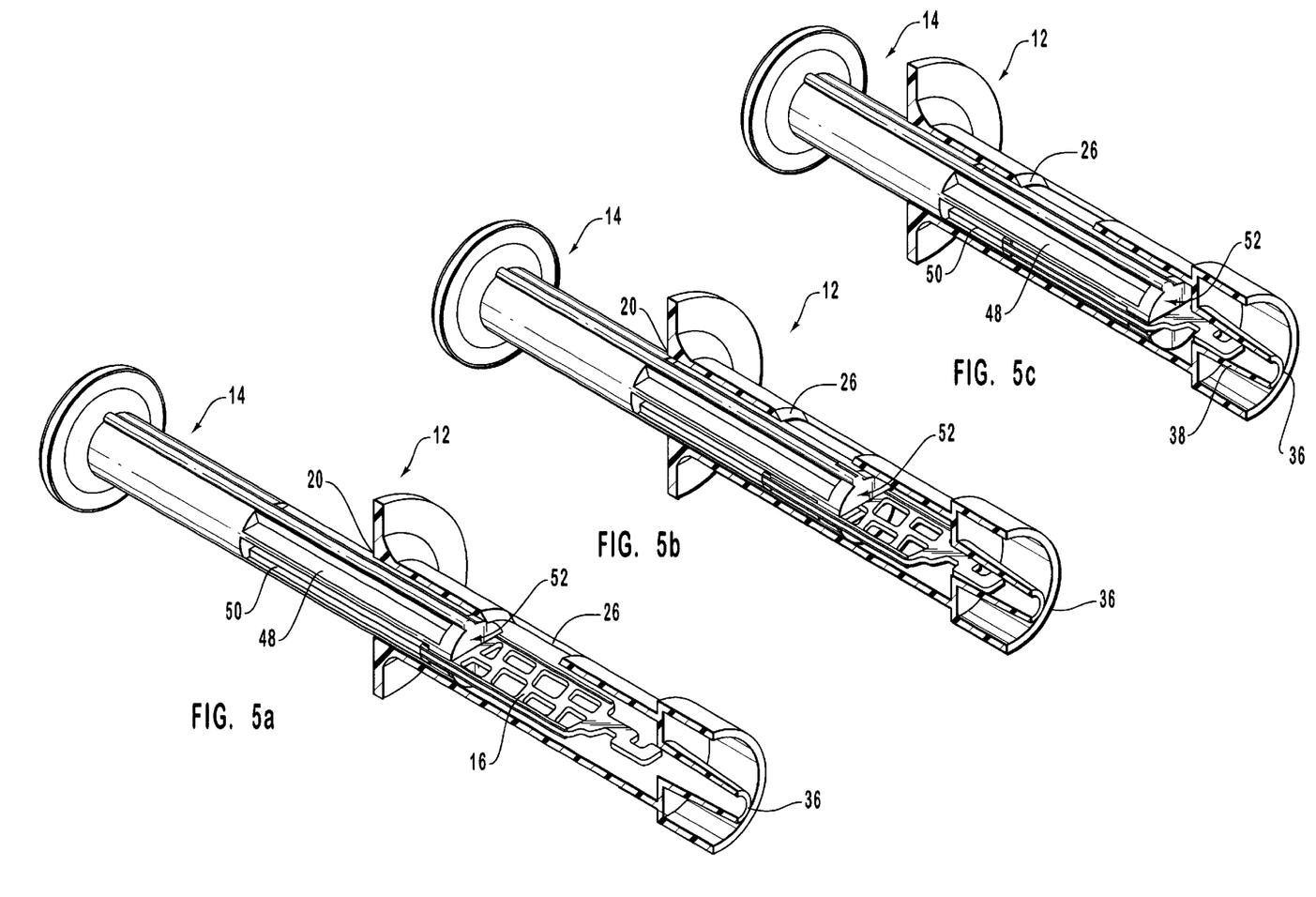
FIG. 5a is a perspective view of the apparatus of FIG. 1 with the plunger slidably mounted partially within the syringe barrel, which is shown in a cutaway view. The paddle is shown in an extended position with respect to the plunger with the distal tip of the plunger located behind the intermediate opening for convenient loading of a composition into the barrel.
FIG. 5b is a view of the apparatus of FIG. 5a with the plunger moved further within the barrel for convenient mixing of a composition within the barrel.
FIG. 5c is a view of the apparatus of FIG. 5a with the distal insertion end of the plunger inserted completely into the barrel such that the paddle is in a contracted position with respect to the plunger.

FIG. 5a demonstrates a view of apparatus 10 in which plunger 14 has been inserted through proximal opening 20 and is partially disposed within barrel 12 with distal tip 52 of plunger 14 located proximal to intermediate opening 26. Paddle 16 is in the extended position. According to one mixing and dispensing technique, material, such as a two-part composition is deposited through opening 26 into barrel 12 while plunger 14 is in the partially loaded, extended position shown in FIG. 5a.

After loading the desired composition, the composition is then mixed by twisting plunger 14 and/or pushing plunger 14 back and forth such that paddle 16 mixes the two-part composition. According to one technique, following loading, plunger 14 is moved distally such that distal tip 52 of plunger 14 is positioned distally from intermediate opening 26, as shown in FIG. 5b. The plunger 14 is then twisted, thereby mixing material within barrel 12 without expelling a substantial amount of material through opening 26.

Upon then pressing plunger 14 further within barrel 12, paddle 16 is compressed into the contracted position (shown in FIG. 5c) within plunger 14 and plunger 14 expresses a mixed composition from distal opening 36. Air escapes from opening 26 as the material is compressed within barrel 12, thereby preventing or at least significantly decreasing the number of air bubbles within the delivered material.

Hollow tip 38 is configured to receive at least a portion of distal tip 82 of paddle 16 when distal insertion end 52 of plunger 14 is pressed distally within barrel 12.

Paddle 16 is preferably comprised of a pliable material such that when a rigid cannula is used, for example, to insert a composition through opening 26 into barrel 12, paddle 16 bends away from the cannula such that additional material may be added into barrel 12. Examples of apparatuses which can be employed to deposit two-part compositions through opening 26 into barrel 12 are featured in U.S. Pat. Nos. 5,643,206; 5,665,066; 5,697,903; and 5,328,462, to Dan E. Fischer, each of which are incorporated herein in their entirety by reference. In a presently preferred embodiment, paddle 16 and plunger 14 are comprised of polypropylene. It will be appreciated, however, that plunger 14 and paddle 16 may be comprised of a variety of different materials.

Paddle 16 is an example of mixing means for selectively mixing a composition within barrel 12. Examples of other mixing means which are movably coupled to the insertion end of the advancing means include paddles which are not perforated, paddles which are completely flat, paddles which are square or circular in shape, and other structures which can accomplish the function of mixing a material. A variety of other plungers and paddles may alternatively be employed in the present invention.

Apparatus 10 may be employed to effect rapid mixing of the composition within the syringe barrel. In order to mix the composition, plunger 14 is merely twisted and/or moved back and forth in a rapid manner prior to pressing plunger 14 further into barrel 12. As one advantage to apparatus 10, it is possible to use plunger 14 and paddle 16 without requiring the continual insertion and retraction of different instruments.

Although a variety of materials may be mixed in the present invention, examples of materials for which apparatus 10 may be useful include resins, sealants, cements, impression materials, and other two-part compositions which may be mixed and delivered according to the present invention.

Plunger 14 is an example of advancing means for advancing a composition within a barrel by movably coupling with the barrel. A variety of other examples of advancing means exist, including plungers having different shapes or configurations.

Figure 7:
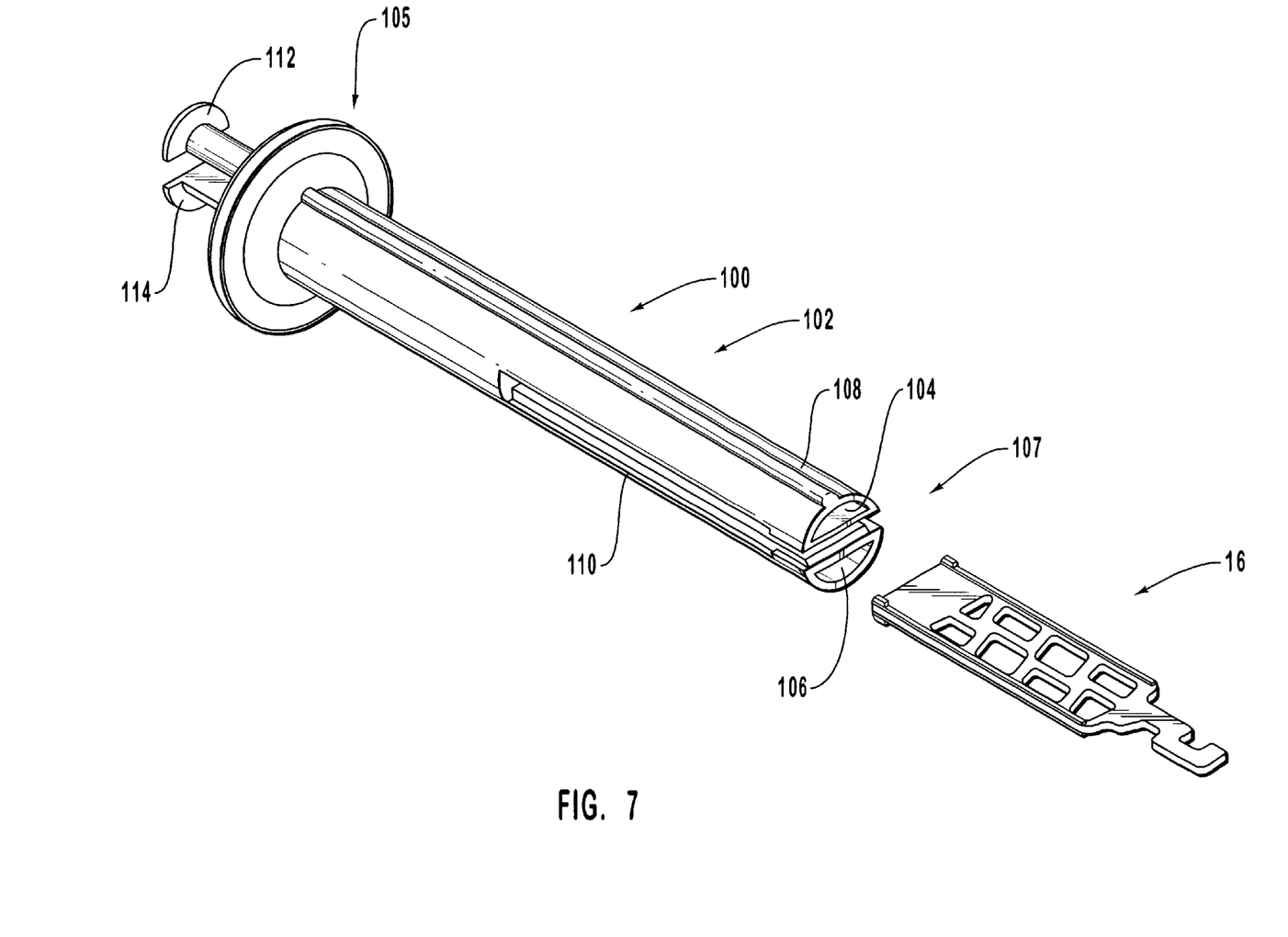
FIG. 7 is a view of an alternate apparatus of the present invention.

With reference now to FIG. 7, in one alternative embodiment, a plunger 100 has a plunger body 102 having first and second hollow passageways 104, 106 extending longitudinally therethrough. Passageways 104, 106 extend from a proximal end 105 of body 102 to a distal end 107 of body 102 and terminate in respective upper and lower fingers 108, 110. A first sub-plunger 112 is received within first passageway 104 while a second sub-plunger 114 is received within second passageway 106. First and second passageways 104, 106 can be loaded with different materials, for example.

Upon desiring to mix and deliver the different materials, plunger body 102 is inserted into a barrel, such as barrel 12 or another barrel which does not have an intermediate opening. First and second sub-plungers 112, 114 are then pressed further into passageways 104, 106, expelling the different materials into the barrel. A paddle, such as paddle 16, disposed between upper and lower fingers 108, 110 is then employed to mix the two-part material. The mixed material can then be delivered from the barrel through a distal opening by pressing the dual-lumen plunger 100 further into the barrel.

Plunger 100 is useful for (i) storing two different materials therein; (ii) delivering the materials therefrom; and (iii) for mixing the materials at a desired time using a paddle disposed between fingers 108, 110. Since plunger 100 can contain both of the different materials, the materials are not required to be added to a barrel before mixing and delivery thereof.

In another embodiment, a plunger of the present invention has a single passageway therethrough and a sub-plunger receivable therein. This single sub-plunger can be useful for delivering one material, while a second material is placed into a barrel in another manner, such as through syringe delivery via an opening such as opening 26. Preferably, however, plunger 100 has first and second passageways therethrough and first and second sub-plungers which are receivable within the respective first and second passageways for delivery of two different materials. Plungers having three or more passageways and corresponding sub-plungers may also be employed.

A slot of the present invention can be configured to slidably receive the proximal end of a paddle in a variety of different manners, such as by having one or more races in the paddle and/or plunger, as shown. Although plunger 14 features first and second races in opposing sides of plunger 14, in an alternative embodiment, a plunger of the present invention has one or more races in a sliding surface of an upper finger thereof, as shown in the plunger 120 of FIG. 8, or in an upper finger and lower finger thereof.

In one embodiment, plunger 100 is employed having passageways 104, 106 filled with desired materials and has first and second plugs (not shown) removably mounted within respective passageways to prevent the materials from seeping out of the passageways prematurely.

Figure 8:
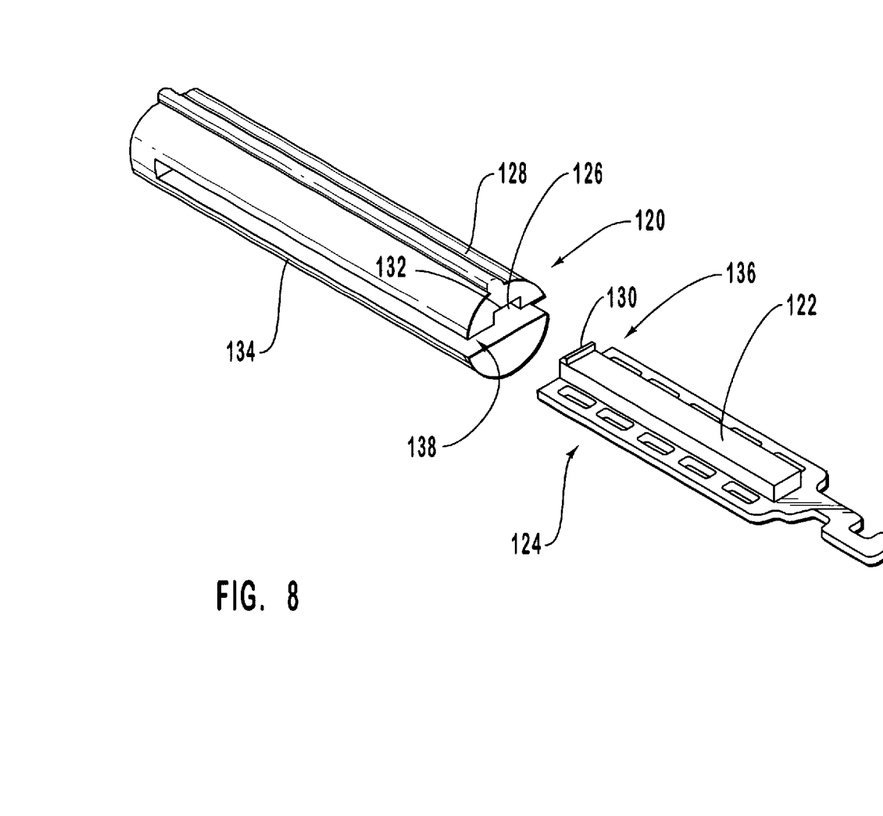
FIG. 8 is a cut-away view of an alternate plunger and paddle of the present invention.

As shown in FIG. 8, in one embodiment, an upper panel 122 extends from a paddle body 124 to slide within a race 126 in a sliding surface of an upper finger 128. A tab 130 extends from panel 122 for engaging a downwardly extending lip 132 which acts as a stop. Optionally, a lower tab or panel (not shown) extends from a panel body 124 to slide within a race (not shown) in a lower finger 134. FIG. 8 thus depicts another example of means for slidably coupling the proximal end 136 of a paddle 124 within a slot 138. Optionally, finger 128 and/or finger 134 can have one or more longitudinally extending grooves (not shown) therein to decrease the mass of the finger(s) and increase the flexibility thereof.

Figure 9:
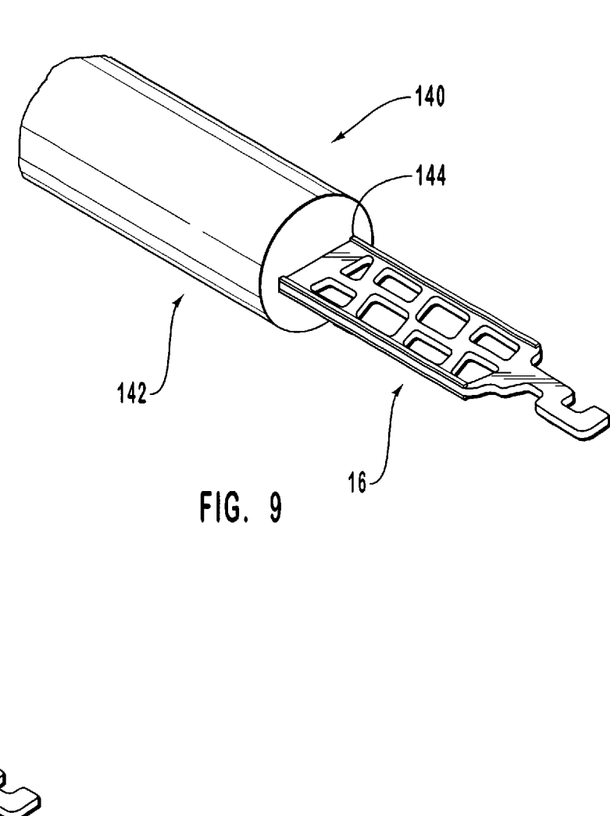
FIG. 9 is a cut-away view of an alternate plunger having a slot in the shape of a bore with the paddle of FIGS. 1–2 slidable therein.

With reference now to FIG. 9, as yet another example of means for slidably coupling the proximal end of a paddle within a slot, a plunger 140 has a plunger body 142 having a slot 144 therein which is configured in the shape of a longitudinal bore or hole which receives proximal end 51 of plunger 16 or another plunger therein. In this embodiment, plunger 140 is configured without separated upper and lower fingers, but instead comprises a one-piece body 142 having bore 144 therein. Proximal end 51 of paddle 16 is slidably coupled to plunger 140 within bore 144. As an example of means for arresting the longitudinal movement of proximal end 51 of paddle 16 within bored slot 144, an internal lip (not shown) within bored slot 144 acts as a stop which engages one or more tabs 90, 92, 94, 95 of paddle 16. The bore or hole may have a variety of different cross-sectional shapes, such as rectangular, square, circular, triangular, other shapes, and/or combinations thereof. Paddle 16 may be inserted into bore 144 through an opening in a proximal end of plunger 140, for example, or by configuring the one or more tabs 90, 92, 94, 95 such that the tabs can be compressed while inserting the tabs past the internal lip, for example.

However, the plungers illustrated are only examples of those which may be employed in order to accomplish the purposes of this invention and a variety of other plungers having a number of different slot configurations are available.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for mixing and dispensing a composition, the apparatus comprising:
a syringe barrel for receiving a composition, the syringe barrel having a proximal opening and a distal opening;
advancing means for advancing a composition within the syringe barrel, the advancing means having a proximal gripping end, a distal insertion end, and an elongate opening formed in the distal insertion end, the distal insertion end of the advancing means being receivable within the barrel; and
a paddle for selectively mixing a composition within the syringe barrel, the paddle being telescopically coupled to the insertion end of the advancing means such that the paddle slides into the elongate opening as the advancing means is advanced into the syringe barrel to dispense the composition out distal opening.

2. An apparatus as recited in claim 1, wherein the syringe barrel has an intermediate opening located between the proximal and the distal openings.

3. An apparatus as recited in claim 1, wherein the advancing means comprises a plunger.

4. An apparatus as recited in claim 1, wherein the plunger has at least one passageway therethrough and a sub-plunger which is receivable within the at least one passageway.

5. An apparatus as recited in claim 1, wherein the plunger has at least one stop located within the slot and the paddle has at least one tab configured to selectively engage the stop.

6. An apparatus as recited in claim 1, wherein the plunger comprises an elongate body having an upper finger and a lower finger extending distally therefrom, the proximal end of the paddle telescopically coupled to the elongate body between the upper and lower fingers.

7. An apparatus as recited in claim 6, further comprising compressing means for compressing the fingers against the paddle.

8. An apparatus as recited in claim 6, wherein the proximal end of the paddle is configured to be slidably coupled to at least one race defined within at least one of the fingers of the plunger such that movement of the paddle between the fingers is substantially linear and such that the proximal end of the paddle is retained in a slidable position between the upper and lower fingers.

9. An apparatus as recited in claim 8, further comprising:
   (i) a stop located at a distal end of the race; and
   (ii) a tab extending from a body of the paddle, the tab configured to engage the stop of the plunger when the paddle is in an extended position, thereby arresting the movement of the paddle along the longitudinal axis of the plunger.

10. An apparatus as recited in claim 1, wherein the mixing means comprises a paddle having a proximal end and a distal end.

11. An apparatus as recited in claim 10, wherein the proximal end of the paddle is slidably coupled within the advancing means.

12. An apparatus as recited in claim 10, wherein the paddle comprises a substantially planar body having at least one tab extending from a proximal end thereof.

13. An apparatus for mixing and dispensing a composition, the apparatus comprising:
a syringe barrel having a proximal opening and a distal opening;
a plunger having a proximal gripping end, a distal insertion end, and an elongate slot formed in the distal insertion end, the distal insertion end of the advancing means being receivable within the barrel; and
a paddle having a proximal end and a distal end and configured to slidably engage the elongate slot, the paddle being movably coupled to the distal insertion end of the plunger such that the proximal end of the paddle slides longitudinally within the slot.

14. An apparatus as recited in claim 13, wherein the syringe barrel has an intermediate opening extending through a wall of the barrel and located between the proximal and distal openings.

15. An apparatus as recited in claim 13, wherein the plunger comprises an elongate body having a slot in the distal insertion end thereof, and further comprising means for slidably coupling the proximal end of the paddle within the slot of the plunger.

16. An apparatus as recited in claim 13, wherein the plunger has at least one stop located within the slot and the paddle has at least one tab configured to selectively engage the stop.

17. An apparatus as recited in claim 13, wherein the plunger comprises an elongate body having an upper finger and a lower finger extending distally therefrom, the proximal end of the paddle movably coupled to the elongate body between the upper and lower fingers.

18. An apparatus as recited in claim 17, further comprising compressing means for compressing the fingers against the paddle.

19. An apparatus as recited in claim 17, wherein the proximal end of the paddle is configured to be slidably coupled to at least one race defined within at least one of the fingers of the plunger such that movement of the paddle between the fingers is substantially linear and such that the proximal end of the paddle is retained in a slidable position between the upper and lower fingers.

20. An apparatus as recited in claim 19, further comprising:
   (i) a stop located at a distal end of the race; and
   (ii) a tab extending from a body of the paddle, the tab configured to engage the stop of the plunger when the paddle is in an extended position, thereby arresting the movement of the paddle along the longitudinal axis of the plunger.

21. An apparatus for mixing and dispensing a composition, the apparatus comprising:
   a syringe barrel having proximal opening and a distal opening;
   a plunger having a proximal gripping end and a distal insertion end, the distal insertion end being receivable within the barrel, the distal insertion end having a slot therein; and
   a paddle having a proximal end and a distal end, the proximal end slidably coupled within the slot of the plunger, the paddle selectively sliding between an extended position and a contracted position with respect to the plunger as the plunger is moved within the barrel.

22. An apparatus as recited in claim 21, wherein the syringe barrel has an intermediate opening extending through a wall of the barrel and located between the proximal and distal openings.

23. An apparatus as recited in claim 21, wherein the barrel comprises:
   a barrel body having a proximal end and a distal end;
   a distal face coupled to the distal end of the barrel body, the distal face having an opening therethrough; and
   a hollow tip extending distally from the distal face, the hollow tip in fluid communication with the barrel body, the hollow tip being configured to receive at least a portion of a distal tip of the paddle when the distal insertion end of the plunger is pressed distally within the barrel.

24. An apparatus as recited in claim 21, wherein the proximal end of the paddle is configured to be slidably coupled to at least one race defined by the plunger, such that sliding movement of the paddle within the slot is substantially linear.

25. An apparatus as recited in claim 24, wherein the paddle has a tab extending from a body thereof, the tab configured to abut against a stop located within the race of the plunger when the paddle is moved to the extended position.

26. An apparatus as recited in claim 21, wherein the plunger has first and second passageways therethrough and first and second sub-plungers configured to be received within the respective first and second passageways.

27. An apparatus as recited in claim 26, wherein the plunger comprises an elongate body having an upper finger and a lower finger extending distally therefrom, the proximal end of the paddle movably coupled to the elongate body between the upper and lower fingers, and wherein the first passageway terminates in the upper finger and the second passageway terminates in the lower finger.

* * * * *